(12) United States Patent
Hasan et al.

(10) Patent No.: US 8,639,531 B2
(45) Date of Patent: Jan. 28, 2014

(54) SYSTEM FOR COMMUNICATION OF HEALTH CARE DATA

(75) Inventors: Malik M. Hasan, Las Vegas, NV (US); J Dominic Wallen, Tucson, AZ (US)

(73) Assignee: HealthTrio LLC, Centennial, CO (US)

( * ) Notice: Subject to any disclaimer, the term of this patent is extended or adjusted under 35 U.S.C. 154(b) by 0 days.

(21) Appl. No.: 12/760,794

(22) Filed: Apr. 15, 2010

(65) Prior Publication Data
US 2010/0241458 A1 Sep. 23, 2010

Related U.S. Application Data

(63) Continuation-in-part of application No. 10/381,158, filed as application No. PCT/US01/42618 on Oct. 11, 2001, now Pat. No. 7,720,691.

(60) Provisional application No. 60/239,860, filed on Oct. 11, 2000.

(51) Int. Cl.
*G06Q 10/00* (2012.01)
*G06Q 50/00* (2012.01)

(52) U.S. Cl.
USPC .................................. 705/3; 705/2

(58) Field of Classification Search
USPC .......................................... 705/2, 3
See application file for complete search history.

(56) References Cited

U.S. PATENT DOCUMENTS

| | | | | |
|---|---|---|---|---|
| 4,491,725 A * | 1/1985 | Pritchard | ............................ | 705/2 |
| 5,890,129 A * | 3/1999 | Spurgeon | ............................ | 705/4 |
| 6,208,973 B1 * | 3/2001 | Boyer et al. | ........................ | 705/2 |
| 6,453,297 B1 * | 9/2002 | Burks et al. | ........................ | 705/3 |
| 6,826,536 B1 * | 11/2004 | Forman | ............................ | 705/4 |
| 7,668,738 B2 * | 2/2010 | Wiggins | ............................ | 705/4 |
| 8,327,020 B1 * | 12/2012 | Sarathi et al. | .................. | 709/239 |
| 8,489,415 B1 * | 7/2013 | Ringold | ............................ | 705/2 |
| 2001/0032099 A1 | 10/2001 | Joao | | |
| 2005/0288964 A1 | 12/2005 | Lutzen et al. | | |
| 2006/0064320 A1 | 3/2006 | Postrel | | |
| 2008/0052124 A1 | 2/2008 | Goodman et al. | | |
| 2010/0042440 A1 | 2/2010 | Joao | | |

OTHER PUBLICATIONS

International Search Report; Jun. 22, 2011.
New Zealand Decision of Assistant of Commissioner of Patents, Feb. 9, 2012.
Tom Pullar-Strecker; US attacks computer patents; Fairfax NZ News; Stuff.co.nz; http://www.stuff.co.nz/business/world/6723386/US-attacks-computer-patents, Apr. 11, 2012.
Amended Notice of Opposition to Grant of Patent; dated Nov. 2010; 2 pages.
Second Amended Statement of Case; dated Nov. 2010; 19 pages.
Declaration Bowden; dated Nov. 2010; 123 pages.
Declaration Cowie; dated Oct. 19, 2010; 2 pages.

(Continued)

*Primary Examiner* — Michael Fuelling
(74) *Attorney, Agent, or Firm* — Barnes & Thornburg LLP

(57) ABSTRACT

A system for transmitting healthcare data from a provider to one of a plurality of healthcare payers is provided. The system includes a routing system, and routing engine. The routing engine is in communication with at least one provider computer system and a plurality of healthcare payer computer systems. The routing engine is configured to receive uploaded healthcare data from the provider computer system send the data to one of the plurality of healthcare payer computers.

5 Claims, 8 Drawing Sheets

(56) References Cited

OTHER PUBLICATIONS

Declaration Desai No. 1; dated Mar. 12, 2010; with Exhibits SD-1 to SD-5; 43 pages.
Declaration Desai No. 2; dated May 10, 2010; 5 pages.
Declaration Faull; dated Oct. 21, 2010; with Exhibit KF1; 15 pages.
Declaration Hasan; dated May 7, 2010; 2 pages.
Declaration McKenzie; dated Oct. 28, 2010; 2 pages.
Declaration Parry No. 4; dated Nov. 2, 2010; with Exhibits DTP16 to DTP21; 74 pages.
Declaration Prib; dated May 11, 2010; 10 pages.
Desai No. 2 Exhibit Exhibit SD-6; dated May 10, 2010; 44 pages.
Amended Notice of Opposition (MOH); dated Nov. 2010; 2 pages.
Second Amended Statement of Case (MOH); dated Nov. 2010; 19 pages.
Oakes Exhibit E1; SolNet ACC version 1.4; Functional Specification for Phase 1 Electronic Messaging Gateway Baseline Deployment; dated Jun. 16, 2000; 62 pages.
Oakes Exhibit E2; EMG Functional Specification; Microsoft Internet Explorer 5; dated Jun. 16, 2000; 38 pages.
Oakes Exhibit E3; EMG Functional Specification; dated Jun. 16, 2000; 43 pages.
Oakes Exhibit F; SolNet ACC Version 1.0 EMG Administration Guide for ACC45 eClaims; dated Jun. 28, 2000; 33 pages.
Oakes Exhibit G; Electronic Messaging Gateway Electronic ACC45 Claims, Business Technology Operations Procedures; dated Jun. 2000; 42 pages.
Oakes Exhibit H; SolNet ACC Version 1.0 User Guide for ACC45 eClaims; dated Jun. 7, 2000; 40 pages.
Oakes Exhibit I; SolNet Professional Services; EMG Functional Specification; dated Jun. 16, 2000; 33 pages.
Oakes Exhibit J; ACC Injury Claim Form; dated Jul. 7, 2008; 8 pages.
Parry No. 1 Exhibits DTP1 to DTP9; Curriculum Vitae of David Parry; 111 pages, 2008.
Parry No. 2 Exhibits DTP10 to DTP14; dated 1996; 49 pages.
Prib Exhibit JPP-1; Personal Data; dated May 11, 2010; 4 pages.
Prib Exhibit JPP-2, dated May 11, 2010; High Court Amendment Rules 2002; 2 pages.
Prib Exhibit JPP-3, dated May 11, 2010; Corrected Version WO 2002/031738 A1; 44 pages.
Prib Exhibit JPP-4; dated May 11, 2010; The Relational Model for Database Management; 24 pages.
Prib Exhibit JPP-5; dated May 11, 2010; An Introduction to Database Systems; 33 pages.
Koch/Loney; Oracle8: The Complete Reference; dated 1997; 155 pages.

\* cited by examiner

SYSTEM FOR COMMUNICATION OF HEALTH CARE DATA

RELATED APPLICATION

The present application is a continuation-in-part application of and claims priority to U.S. patent application Ser. No. 10/381,158 filed Mar. 21, 2003, entitled "System for Communication of Health Care Data" which claims priority to PCT Application No. PCT/US01/42618 filed Oct. 11, 2001, entitled "System for Communication of Health Care Data" which claims priority to U.S. Provisional Patent Application Ser. No. 60/239,860, filed Oct. 11, 2000, entitled "Apparatus and Method for Establishing Connectivity." To the extent not included below, the subject matter disclosed in this application is hereby expressly incorporated into the present application.

FIELD OF THE INVENTION

The present invention relates generally to a computerized system that establishes connectivity between interested parties in the health care industry for the administration of health care services. More particularly, the present invention relates to a system for the normalization of health care data of various formats and exchanging the data in normalized form between insurers and participants, such as providers, patients, and employers.

BACKGROUND AND SUMMARY

Health care can be defined as an information industry; most of the time and money spent in procuring and delivering health care is spent creating, retrieving, or using information. Expenditures on health care information technology support, for example, have increased from about one billion dollars in 1990 to a projected $20 billion in 2000. Yet, even with these investments, it is believed that almost half of all current health care expenditures continue to be for non-patient care activities; a major share of which is for non-automated information support.

Resources having to be directed to non-patient care activities have been endemic in the health care industry since the 1960's. During the 1990's, however, with the demise of Medicare Cost Reimbursement and the rise of managed care, there has been a major shift in attitude and focus among both physicians and patients. New rules now govern the delivery of medical care and the payment for such care. Whether via preferred provider arrangements, capitation arrangements of endless variety, case management, or "best practice" enforcement, determining what care is allowed, what will be paid by whom, and making sure that the appropriate information is submitted to ensure that the process works are now consuming a major share of both time and financial resources of insurers, providers, and patients.

Health care participants, like providers and employers, regularly deal with a number of health care plans from various health insurers. These participants, however, can only obtain information from the insurance companies in limited ways, often making the acquisition of such information quite burdensome. Participants usually only have the telephone, fax, or letter available as a means of communication with the insurers.

Particularly vexing is the timely availability of information from insurers regarding financial transactions, such as eligibility, claims, and benefits, and basic patient-related information, such as medical tests and prescriptions. For example, a provider may seek information from an insurer via a submission form or telephone call to that insurer. In many cases, however, such information is sought or received after the care has been delivered and the patient has left the provider's office. This may result in the delivery of services that are not authorized or covered by the patient's insurer, or may result in other consequences that might impact the type or cost of the services provided.

Another reason for these difficulties is the recent expansion of the "payer" community. At one time, payers consisted of the government (both federal and state) and large insurance companies. Now, a complex array of self-insured plans, IDN's, IPA's, and PPO's, undertaking full or partial capitation, insurance carve-outs, and the like have radically increased the number of users of, and the need for, current information regarding insureds. Most of these entities, both small and large, do spend considerable sums on information systems. Yet, because of the extent of manual processing that exists despite these systems, costs per claim remain substantial.

In addition, payers incur the wrath of their providers and patients by designing complex rules that are difficult or perceived as impossible to administer or follow. Though contrary to this perception, payers do have an interest in providing timely information to providers, patients, employers, and other participants. Still, a significant percentage of a provider's claims are rejected often because they do not comply with all of the rules. These claims require resubmission, telephone calls, and other expensive manual interventions. The dollar costs for this current processing scheme are high. In fact, an entire clearinghouse industry has been developed to provide eligibility (but not benefits) verification services to providers for a fee. Many of the requested verifications, however, cannot be performed at all by such clearinghouses, and those that are performed are often unacceptably cumbersome and, thus, too expensive.

Referral authorizations are often even more complex than claims and such authorization services are generally not available via traditional clearinghouses. Each time a provider writes a prescription, for example, it is written against a formulary specific to that patient's health care plan established by their insurer. Because there are so many formularies, drug prescriptions, too, are often rejected for payment, causing additional work for both the provider and the patient. Similarly, medical tests must be sent to laboratories contracted to support a particular plan, and are reimbursed only when matching complex medical necessity rules.

Many providers do have practice management systems that track encounters and manages billing. None of these systems, however, have the sophistication to accomplish the task of providing all of the information from all the various health insurers in such a cogent form that can be useful to the provider.

Not only providers, but patients, too, spend a majority of their time interacting with the health care system engaged in non-health care activities. This "wasted" time is virtually all related to scheduling appropriate interventions, to waiting for information or services, or to obtaining authorization, reimbursement, or other information for desired or required health care.

The internet has emerged as a major source of health care information for the public. A substantial portion of internet users use it for health care information or management. Specifically, patients search the internet for medical information and answers related to their area of concern. In fact, it is becoming common for a patient to enter a physician's office armed with printouts and long lists of questions and recommendations from web pages on the internet.

Unfortunately, even with the connectivity the internet provides, information exchange between insurers and patients is lacking. Most of the information available to patients from their insurer is on an automated basis from databases related to either general health care literature or to specific normality support groups. A critical aspect of the patient's health care program, however, is not only knowledge of the normality or support groups, but also what their insurer's health care plan provides as treatment options for that normality, eligibility information, referral authorization, claim submission and payment, testing, and medications. As discussed, these functionalities are too complicated for the current system to handle in an automated environment. Personally-referenced information linked to an individual patient's provider and health care plan is generally unavailable, because that data exists in several databases often each in a different, incompatible format, requiring human intervention to extract and process the data. The patient's current solution is, thus, an endless number of telephone calls at a high cost in dollars, time, and frustration.

A reason for such incompatibility is that each database served the individual needs of those using the data before such a time when connectivity between databases was a consideration. The consequence of having different databases of different formats is that it is not possible to provide a central repository of homogenized data readable by any variety of computers. It is this incompatibility that prevents wide spread connectivity between insurers and participants.

Transliterating and interfacing programs are known in the art. Programs that take data in one format can be translated and read by a computer of a different format. Such transliterating, however, only shifts data from a field of an incompatible format to a target field of a new format. It cannot determine whether the data of the incompatible format is being transferred to the correct target field. Normalization or remodeling of the data not only transfers the data, but also determines the meaning of the data and puts that data in the correct field.

It would, therefore, be beneficial to provide a system with which insurers may communicate with providers, patients, etc., to provide information about a particular health care plan either before, or contemporaneously with, the patient's visit to the provider, regardless the lack of compatibility of the databases. It would be further beneficial if this system of communication spanned a variety of insurers so the provider, for example, may communicate with any plan in which the patient participates. It would also be beneficial for providers to have an automated system of determining eligibility and benefits, receiving authorizations and pre-certifications, submitting claims, obtaining reimbursements, and adjudicating claim problems through the normalization of data of the incompatible databases.

Accordingly, an illustrative embodiment of the present disclosure provides an apparatus for communicating health care data from a sender to a receiver. The apparatus comprises a first computer system, a second computer system, and a rules engine. The first computer system having health care data stored therein. The second computer system is in operable communication with, and is configured to extract the health care data from the first computer system. The rules engine normalizes the extracted health care data to a predefined format. The rules engine defines a plurality of health care data fields in the predefined format, as well as a plurality of relationships between fields of normalized data.

Further embodiments may include the first computer being a plurality of computers each having portions of the health care data stored thereon. The apparatus may also comprise a third computer system, in operable communication with, and configured to receive the normalized data from, the second computer system. The rules engine may determine whether the third computer is authorized to receive the health care data.

Another illustrative embodiment provides a method for communicating health care data from one computer system to another. The method comprises the steps of storing health care data in a first computer system; extracting health care data from the first computer system and communicating the extracted data to a second computer system; normalizing the extracted data to a predefined format in accordance with a rules engine that defines a plurality of health care data fields in the predefined format and a plurality of relationships between fields of normalized data; and communicating the normalized data to a third computer system.

Further embodiments of the illustrative method may include the first computer system comprising a plurality of computers, wherein the storing step includes storing health care data in more than one of said computers. Also, the third computer system comprises a plurality of computers. The health care data exists across a plurality of databases such that each of the plurality of databases are in operable communication with the second computer system.

Another illustrative embodiment provides a system of exchanging health care data between a sender and a receiver. The system comprises a sender computer, an intermediary computer, a rules engine and a receiver computer. The sender computer stores the health care data. The intermediary computer is in operable communication with the sender computer and is configured to extract the health care data. The extracted data is normalized to a predefined format, creating normalized data pursuant to a rules engine. The rules engine defines each field of the health care data and converts each field to a corresponding field in the predefined format. The rules engine also defines how the normalized data should relate to each other pursuant to predetermined instructions. The receiver computer is in operable communication with the intermediary computer. The receiver computer receives the normalized data subjected to the second rules engine.

Further embodiments may include the sender computer being a plurality of computers each having portions of the health care data stored thereon. The rules engine may determine whether the receiver computer is authorized to receive the health care data. When the receiver is a health care provider, the normalized data exchanged between the sender and receiver may be chosen from a group comprising eligibility/benefit display, member roster, claim submission, provider lookup, formulary lookup, diagnosis code lookup, procedure code lookup, access health plan information online, communicate with a health plan on-line, communicate with patients on-line, patient-centric view of data across several health plans, order generation and tracking, results review and release, result printing, prescription writing, medication profile for each patient, access to patient's personal health record based on patient approval, personalized medical and health care content integration, both context-specific and on demand, e-commerce integration: office, medical and health-related product awareness and buying capabilities, email, practice management system subscription, support disease management, and physician credentialing subscription. When the receiver is an employer, the normalized data exchanged between the sender and receiver is chosen from a group comprising group eligibility, group enrollment, enrollment changes, formulary lookup, e-commerce integration, access from health plan web site or direct access via URL, personalized content integration, both context-specific and on demand, e-commerce integration and health care-related product awareness and buying capabilities.

When the receiver is a patient, the normalized data exchanged between the sender and receiver is chosen from a group comprising identification card requests, address changes, provider directory inquiries, personalized health information based on an interest profile, diagnosis information, relevant articles and patient education materials, communications from health care providers and health care plans, lab and radiology results, scheduled appointments with a health care provider, prescription refills, personal health records, eligibility/benefit information, claim information, referral and authorization information and status, provider lookup, family history, medication profile and formulary lookup.

Another illustrative embodiment of the present invention provides a system of normalizing health care data for transfer between an insurer and a participant. The system comprises an insurer system, an intermediary system, and a participant system. The insurer system is configured to maintain at least one database comprising the health care data. The intermediary system is operatively connected to the insurer system and to the database, configured to extract the health care data from the database of the insurer system, and store the health care data in a staging database as extracted data. The extracted data is normalized to a predefined format, creating normalized data pursuant to a rules engine that defines each field of the extracted data in the predefined format. The rules engine also defines how the normalized data relates to each other pursuant to predetermined instructions. The participant system is in operable communication with the intermediary system, and is configured to receive the normalized data subject to the rules engine.

Further embodiments of the illustrative system may include the at least one database being a plurality of databases, such that the intermediary system is operatively connected to the plurality of databases. In addition, the participant system may transmit a request that is sent to the intermediary system that determines which health care data is to be extracted and normalized in order to respond to the request. The participant system may also transmit the request, and the intermediary system may transmit the normalized data over the internet. The rules engine may define the relationships among the normalized data pursuant to predetermined instructions to determine a response to the request. The intermediary system may also comprise an error data system that removes extracted data identified as invalid when the extracted data is normalized. The extracted data identified as invalid is then corrected, reintroduced, and is normalized. The intermediary system may further comprise an audit database to track the activity of the intermediary system.

Another illustrative embodiment of the present invention provides a system of health care management of medical testing administration between an insurer, a medical laboratory, and at least one health care participant. The system comprises a participant computer, an insurer processing system, a rules database, and a laboratory computer. A medical test request is made at the participant computer pursuant to a first predetermined format. The insurer processing system is operatively coupled to the participant's computer, and is through which the medical request is transferred. The processing system is operatively coupled to the rules database to approve the medical test request pursuant to predetermined criteria. The laboratory computer is operatively coupled to the processing system and receives the medical test request if approved by the rules engine. Results of the medical test are transmitted from the laboratory computer to the processing system. The results are further transmitted to an insurer computer that is operatively coupled to the laboratory computer and to participant's computer.

Further embodiments of the illustrative system may include the processing system converting the results of the medical test to a second predetermined format readable by a database stored on the insurer computer. In addition, at least one health care participant may be chosen from a group comprising from a health care provider, an employer, and a patient. Furthermore, the medical test request and the results of the medical test may be transmitted through the internet.

Another embodiment of the present disclosure provides a system for transmitting healthcare data from a provider to one of a plurality of healthcare payers. The system comprises a routing system, and routing engine. The routing system is in communication with at least one provider computer system and a plurality of healthcare payor computer systems. The routing engine is configured to receive uploaded healthcare data in a data file from the provider computer system. The routing engine is also configured to route the healthcare data to the plurality of healthcare payer computers and validate the received data file. This determines whether there are multiple transactions in the data file. If so, the multiple transactions are separated. For each transaction, the routing engine is configured to determine the identity of one of the plurality of healthcare payer computers. A healthcare payer configuration file containing identities and routing addresses of the healthcare payer computers can pair the transactions with their corresponding healthcare payer computers. The routing engine is further configured to send the transactions to the corresponding healthcare payer computers.

In the above and other embodiments the system may also comprise healthcare data from the provider being transmitted to the routing system as the data is being entered from the provider, and wherein that entered data is then distributed to the corresponding payers; selected healthcare data being extracted from the data files to populate a personal or electronic health record; and rules can be applied to select certain healthcare data including demographic data, visit/encounter information, conditions and illnesses, surgeries and procedures, medication information, lab and other types of results, immunization information, clinical notes and summaries, such as discharge summaries.

Additional features and advantages of the system will become apparent to those skilled in the art upon consideration of the following detailed descriptions exemplifying the best mode of carrying out the system as presently perceived.

BRIEF DESCRIPTION OF THE DRAWINGS

The illustrative system will be described hereinafter with reference to the attached drawings which are given as non-limiting examples only, in which.

Corresponding reference characters indicate corresponding parts throughout the several views. The exemplification set out herein illustrates an embodiment of the invention, and such exemplification is not to be construed as limiting the scope of the invention in any manner.

DETAILED DESCRIPTION OF THE DRAWINGS

Figure 1:
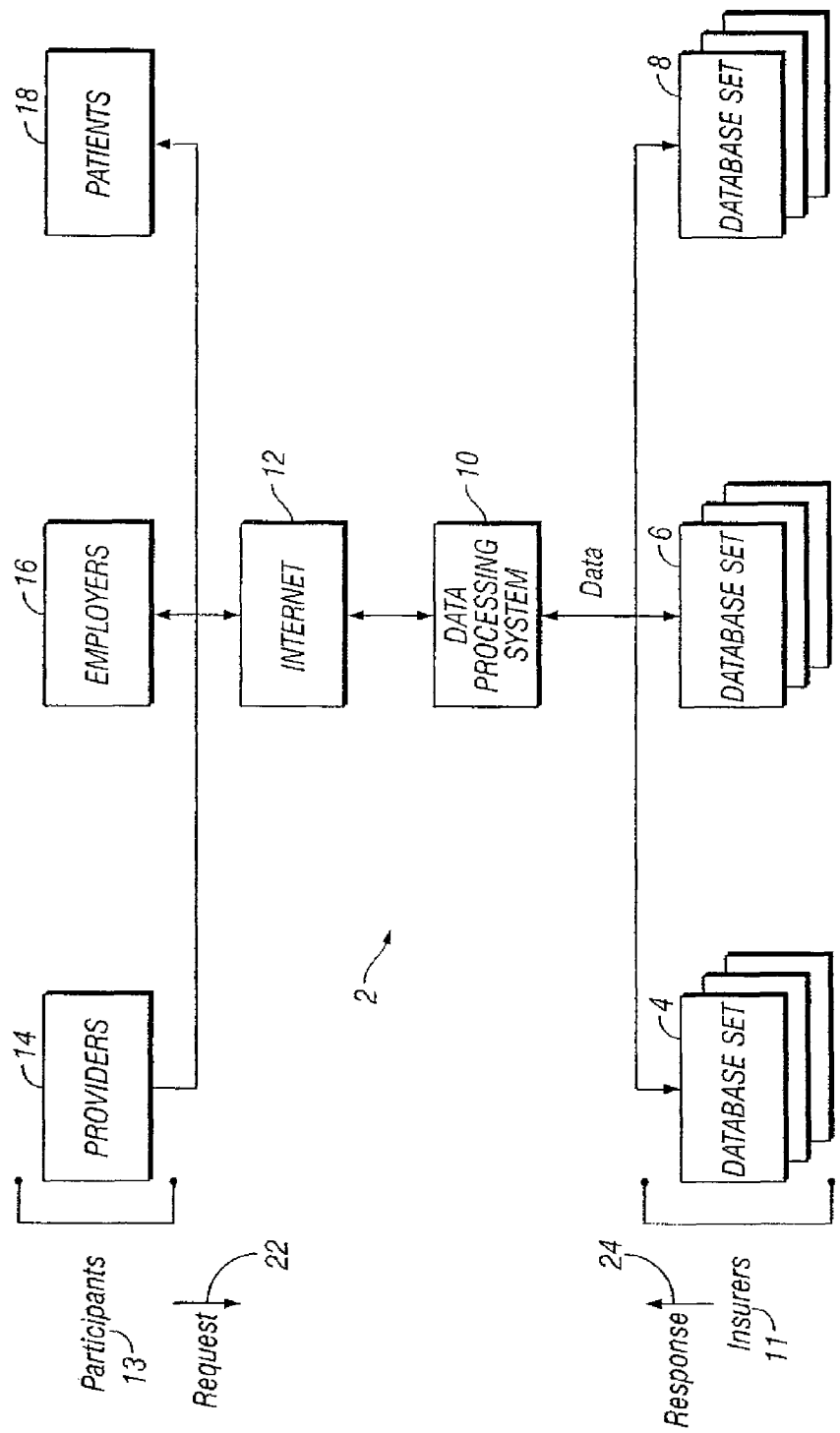
FIG. 1 is a diagrammatic view of a system for normalization of health care data and the exchange of same between several health care insurers and various health care participants.

An illustrative embodiment of the invention, such as that shown in FIG. 1, comprises a system 2 which includes a plurality of database sets 4, 6, 8 offered by a variety of insurers 11. It is appreciated that each health care database set 4, 6, and 8 represents an insurer's database processing system or series of processing systems and databases. For example, database sets 4, 6, or 8 may each represent a conventional computer system, a server, a local area network (LAN), a legacy, or other computer system storing one or more databases. It is contemplated that to transmit data, either the system as it exists is capable of doing so, or a system is added to either database sets 4, 6, or 8 to perform this function. It is further contemplated that each of database sets 4, 6, 8 may represent a single database or a plurality of databases, each of which may be of any variety of database formats or languages.

For the purposes of this application, it is contemplated that reference to the term "insurer," as used herein for insurers 11, is for illustrative purposes only. Such a term includes health insurance companies, but also includes health maintenance organizations, self-insured entities, disease management organizations, capitated health care providers, Medicare agencies, as well as any other organization that might store or manage health care data. The term "insurer" is not to be construed as being limited in scope to only health insurance companies or other "payers."

Conventionally, health care data is stored on an insurers' computer or series of computers in several databases, each of which often being in a unique format, with each database format being incompatible with other database formats. For example, one insurer may have their health care data stored in one format, and a second insurer may have their health care-related data stored in a second format that is not compatible with the one format. Additionally, and more problematic is that, even within the same insurer's 11 system, eligibility data, for example, may exist in a database of one particular format, developed to suit the needs of its users at the time, whereas, the claims data, for example, may be stored in another database in a format that suits the needs of those users, but with its format being incompatible with the format of the eligibility data. In either example, it is contemplated that in the present invention, health care data of any format is normalized into a common format, and distributed through a common network, like internet 12, to a health care participant 13, who uses the normalized data to conduct health care-related transactions and tasks. It is further contemplated, and to be discussed further herein, that various levels of access and security can be provided to assure that those participants 13 accessing the normalized data are authorized to access only that data predetermined as necessary and appropriate for their particular use or need.

As FIG. 1 shows, data from each database set 4, 6, 8 can be transmitted to a data processing system 10 that normalizes the data into a format readable by particular health care participants 13. More specifically, the data is transmitted over the internet 12, which is operatively connected to and read by participants' 13 computer(s) or terminal(s). Such participants 13 illustratively include providers 14, employers 16, and patients 18, or any combination thereof. It is contemplated that participants 13 can further include any other interested party that can request data or information from an insurer, including other insurers and disease management organizations, for example.

It is contemplated that the transmission of data from database sets 4, 6, or 8 is initiated by any of the participants 13 submitting a request 22 through a computer or computers. Request 22 is transmitted through the internet 12 to data processing system 10 which retrieves the appropriate data from the appropriate database set or sets of either 4, 6, or 8. That data is normalized to a common format, at which point a response 24 to the request 22 is made. For example, a health care provider 14 may place a request 22 on behalf of an insured to authorize payment for a medical procedure. In this example, it is presumed that the data required to formulate a response 24 exists collectively on eligibility, benefits, and claims databases that illustratively exist on database set 4. Data processing system 10, in order to prepare a response 24, determines and extracts which data is necessary from the databases. System 10 then normalizes the data into a homogenous format, and then determines what the nature of the response should be. In this example, response 24 should be to either authorize or deny payment for the medical procedure. System 10 uses the normalized data to determine the response, which is then transmitted to provider 14, thus, completing the transaction. It is contemplated that system 2 may comprise any number of insurers 11 or participants 13. Specifically, data processing system 10, as will be discussed further herein, is able to connect and manage transactions between a single or plurality of participants 13 with any insurer or plurality of insurers 11.

It is further contemplated that system 2 will provide health care participants 13 with a variety of health care transaction options referred to generally in the form of requests 22 and responses 24 between participants 13 and insurers 11. Examples of transactions available to health care providers 14 are: eligibility/benefit display, member roster, claim submission, provider lookup, formulary lookup, diagnosis code lookup, procedure code lookup, access health plan information online, communicate with a health plan on-line, communicate with patients on-line, patient-centric view of data across several health plans, order generation and tracking, results review and release, result printing, prescription writing, medication profile for each patient, access to patient's personal health record based on patient approval, personalized medical and health care content integration, both context-specific and on demand, e-commerce integration: office, medical and health-related product awareness and buying capabilities, email, practice management system subscription, support disease management, and physician credentialing subscription.

As further example, the following are specific records and fields for health care transactions between providers 14 and insurers 11 that utilize normalized data:

Record: Summary
_Fields:
  Activity for (date)
  Referrals
  Claims
  Test Results
  Members
  Update State for Americas Health
  Benefit Records
  Claim Records
  Patient Records
  Provider Records
  New Just For You
Record: Eligibility
_Fields:
  Today's Patients
  Patient Search
  Sex
  Coordination of benefits
  Medicare data
  Add to patient list
  Name
  From Date
  To Date
  Birth date
  Member ID
  Relation
  PCP
  Address
  City
  State
  Zip
  Current Benefit
  Group
  Carrier
  Benefit Plan
Record: Claim Status
_Fields:
  Patient Name
  From Date
  To Date
  Claims
  Claim Number
  Status
  Provider Name
  Patient Name
  Member Number
  Billed Amount
  Patient Responsibility
  Paid Amount
  Date of Service
Record: Claim Detail
_Fields:
  Member
  Provider
  Diagnosis
  Description
  Line number
  DOS
  CPT
  Description
  Modifier
  Location
  Units
  Status
  Billed
  Allowed
  Copay
  Coinsurance
  Deductible
  Paid
  Totals
Record: Explanation of Payments
_Fields:
  Line Number
  Status Description
  Explanation
  Check/Date
Record: Select Specialist
_Fields:
  Address
  City, State, Zip
  Handicap Access
  Office Hours
  Contact
  Phone
  Fax Phone
  Phone After Hours
  Sex
  Birth Date
  Specialty
  Second Specialty
  Accept Patient
  Primary Care
  Board Cert
  Languages
  Hospitals
  Hospital Privileges
  Networks
Record: Add Claims
_Fields:
  Health Insurance
  Insured's ID Number
  Patient Last Name
  First Name
  Middle Name
  Patient's Address 1
  Address 2
  City
  State
  Zip
  Patient's Phone
  Birth date
  Gender
  Relationship to Insured
  Marital Status
  Patient Employment Status
  Condition Related to Job
  Con. Rel. to Auto Accident
  Cond. Rel. to Other Accident
  Insured's Last Name
  First Name
  Middle Name
  Gender
  Birth date
  Insured's Address 1
  Address 2
  City
  State
  Zip
  Phone Insured's Group or FECA Number
Insured's Employer/School
Insured's Insurance Name
Referring Physician Name
Referring Physician ID
Outside lab
Outside Lab Charges
Medicaid Resub Code
Medicaid Orig.
Prior Auth. Number
Diag Codes
Item
Date From
Date To
Place
Type
Procedure
Mod1
Mod2
DX Ind.
Charges
Days/Units
Patient
Provider
From Date
To Date
Diagnosis 1
Diagnosis 2
Diagnosis 3
Diagnosis 4
Procedure Line
CPT
Description
Amount
Dx pointer
Other Errors
Total Amount
Billed
Allowed Amount
Copay Amount
Withheld Amount
Writeoff Amount
Predicted Payment
Record: Referral Status
_Fields:
  Referral Number
  Patient (Member ID)
  Valid from (months)
  Referred by
  Referred to
  Patient List
  Referred by
  Referred to
  Referral Number
  Status
Record: Add Referrals
_Fields:
  Today's Patients
  Patient Search
  Specialists
  Specialist Search
  Providers
  Diagnosis
  Patient
  Specialists
  Provider
  Diagnosis
  Start Date
  Months Valid
  Visits Requested
  Reason
Record: Procedure and Diagnosis Data
Fields:
  Diag Number
  Diagnosis Name
  Proc Code
  Procedure Name
  Visits Allowed
  Patient
  Patient Search
  Referred to
  Specialist Search
  Referred by
  Diagnosis
  Start Date
  Exp Date
  Visits Requested
  Remarks
  Services Requested
  Authorized Ancillary Services
Record: Diagnosis Codes
_Fields:
  Diagnosis Code
  DX Code
  Diagnosis Code Description
  Record: Procedure Codes
_Fields:
  Procedure Codes
  Procedure Code
  Procedure Description
  Age From
  Age To
  Sex
  Location Code
Record: Drug Therapeutic Class Listing
_Fields:
  Therapeutic Class
  Class Description
  Count of Drugs in this Class
Record: Formulary List by Therapeutic Class
_Fields:
  Drug Name
  Generic Name
  Drug Class
  Therapeutic Class
  NDC
Record: Write Prescription
_Fields:
  Today's Patients
  Patient Search
  Providers
  For
  Medication
  Dispense
  Refill
  Sig: Take
  Sig: For
  Instructions
  Select Pharmacy
Record: Medication Profile
_Fields:
  Type
  Medication
  Dose Frequency
   Reason
   Status
Record: Discontinued Medications
 _Fields:
   Type
   Medication
   Dose
   Frequency
   Reason
   Status
Record: Allergies
 _Allergen
   Reaction
   Date Started
Record: Medical Test Orders
 _Fields:
   Patient ID
   Patient Name
   Provide ID
   Provider Name
   Location
   Lab Name
   Dx
   Action
   Battery
   Test
   ID
   Type
   Volume
   Date
   Time
   Collected By
   Chemistry
   Hematology
   Toxicology/Therapeutics
   Microbiology/Virology
   Immunology/Serology
   Urinalysis/Fluids
   Procedure
   When
   Priority
   Specimen
   Alert
Record: Results
 _Fields:
   Status
   Order number
   Test Procedure
   Alert
   Order Date
   Facility
   Patient
   Provider
   Date/Time
   Procedure
   Status
   Indicator
   Date/Time
   Performed
   Specimen Number
   Type
   Status
   Result
   Value
   Desired Range Each field listed above represents data that can exist anywhere on database sets 4, 6, or 8, and be in any format or language. If any request 22 is made which calls up one or more of the above records, data processing system 10 searches, extracts, and normalizes the data so it appears in the correct field in the record. It is appreciated that provider 14 may change the data, if necessary, and transmit it back through internet 12 and data processing system 10 to be stored on the appropriate database set 4, 6, or 8.

Examples of transactions available to employers 16 are: group eligibility, group enrollment, enrollment changes, formulary lookup, e-commerce integration, access from health plan web site or direct access via URL, personalized content integration, both context-specific and on demand, e-commerce integration: human resource, business (e.g., office supplies) and health care-related product awareness and buying capabilities.

Again, as a further example, the following are specific records and fields for health care transactions between employers 16 and insurers 11 that utilize normalized data:
Record: Open Enrollment
 _Fields:
   Health Insurance
   Employer Group Number
   Last Name
   First Name
   Middle Name
   Employee Address 1
   Address 2
   City
   State
   Zip
   Home Phone
   Work Phone
   Primary Language
   Birth date
   Gender
   Social Security Number
   Primary Care Physician
   Established Patient
   Dependent Last Name
   First Name
   Middle Initial
   Birth date
   Gender
   Relationship
   Social Security Number
   Primary Care Physician
   Established Patient
   Effective Date
   Hire/Rehire Date
   Other Health Care Policy
   Name and Address of Insurer
   Effective date of other coverage
   Policy Holder's Last Name
   First Name
   Middle Name
   Policy/Group Number
   Covered by Medicare
   Medicare Number(s)
   Health insurance within the last 18 months
   If yes, type of coverage: group, individual, COBRA, Medicare/Champus, Conversion or Other
   Reason coverage was terminated
   Read and Agree to Authorization Statement Record: Enrollment—Changes
_Fields:
  Health Insurance
  Employer Group Number
  Last Name
  First Name
  Middle Name
  Employee Address 1
  Address 2
  City
  State
  Zip
  Home Phone
  Work Phone
  Primary Language
  Birth date
  Gender
  Social Security Number
  Primary Care Physician
  Established Patient
  Term Member
  Dependent Last Name
  First Name
  Middle Initial
  Birth date
  Gender
  Relationship
  Social Security Number
  Primary Care Physician
  Term Dependent
  Hire/Rehire Date
  Effective Date
  Change Reason
  Name
  Enrollment Type
  Remarks Examples of transactions available to patients 18 are: identification card requests, address changes, provider directory inquiries, and personalized health information based on the member's interest profile, as well as diagnosis information from health plan administrative and clinical information, relevant articles and patient education materials, communications from health care providers and health care plans, lab and radiology results to patients online, scheduled appointments with a health care provider, referral status, prescription refills, education materials, personal health records so it can be maintained in his or her comprehensive health history online for physician reference, view eligibility/benefit information, view claim information, view referral and authorization information, provider lookup, personal health record, family history, medication profile, formulary lookup, and communications between member and provider.

Figure 2:
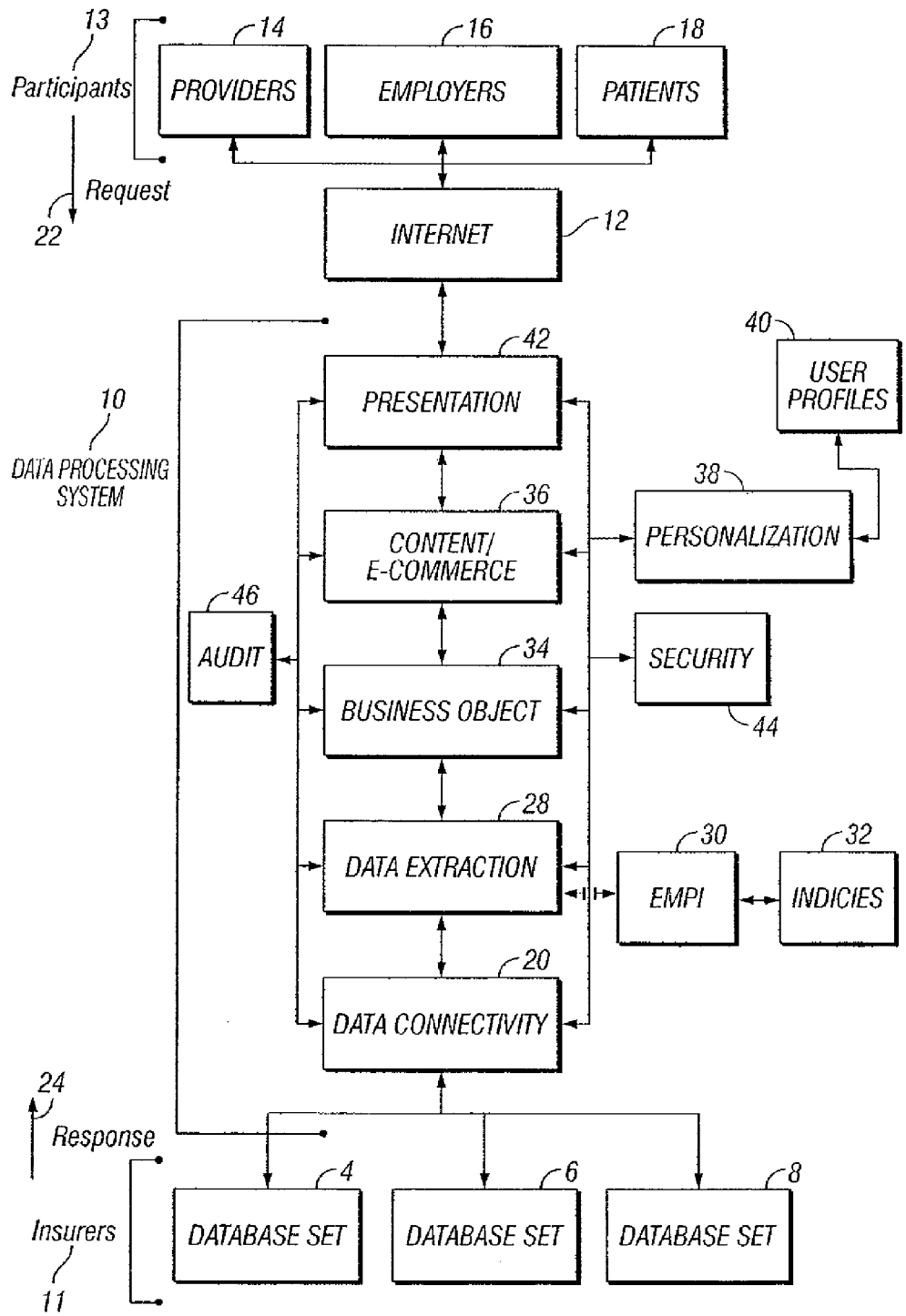
FIG. 2 is a diagrammatic view of the data processing system for the system of normalization shown in FIG. 1.

The architecture of the data processing system 10 is shown in FIG. 2. Each of the database sets 4, 6, 8 is operatively connected to data connectivity sub-system 20. The data connectivity sub-system 20 is configured to receive the different types of connections used between the various computer systems which store the database sets 4, 6, 8. It is appreciated that, in other embodiments, a separate data processing system 10 may be provided at the site of each of the database sets 4, 6, 8 such that each data processing system 10 is dedicated to manage and normalize the data, as discussed further herein, as well as manage server-to-server communications for a single database set.

The data extraction sub-system 28 is also depicted in FIG. 2. Sub-system 28 manages the integration of the often plurality of databases. The data extraction sub-system 28, as further discussed in reference to FIG. 3, also includes logic to manage data access from the several databases of database sets 4, 6, 8. An enterprise master person index ("EMPI") 30 is operatively coupled to data extraction sub-system 28. The EMPI 30 presents a cross-database view of all the insureds within system 2. It also manages the proper identification of providers 14, employers 16, connected patients 18, as well as other entities having unique identities on an as-needed basis. An indices database 32 is supported by EMPI 30. Specifically, the indices database 32 stores indices which serve as a basis for relating the identification data to each other. The indices database 32 is typically built upon and maintained by the EMPI 30.

The business object sub-system 34 contains the logic rules that drive the normalization of data and use of same between insurers 11 and participants 13. To provide such capabilities, a variety of processes may be supported in any particular situation. Illustratively, such processes may include, but are not limited to, rules-based evaluation of entered data for referral authorizations and admission pre-certifications; proxy or actual adjudication of claims submitted by providers, with concomitant delivery of funds to insurers 11 and benefits explanations to patients 18; sorted lists of providers 14, employers 16, and patients 18; and graphical displays of laboratory results and integrated claims-driven health records for patients 18.

The content/e-commerce sub-system 36 adds third party capabilities to the data processing system 10. The content portion of sub-system 36 provides management and integration of third party affiliated content, such as articles about diseases, bulletins, notices, notes, and other medically-related references. The e-commerce portion of sub-system 36 integrates e-commerce capabilities, including business-to-business or business-to-consumer purchasing through shopping cart-type databases with affiliated product and service vendors.

The personalization sub-system 38 integrates information from the previous sub-systems 20, 28, 34, 36 to provide a personalized view of data in system 2. Specifically, when any of the participants 13 login to system 2 and access data or other information from database sets 4, 6, or 8, or even the content/e-commerce sub-system 36, pertinent information derived from the type of content viewed, as well as the products purchased or searched, is maintained in a user profile database 40. During subsequent logins, therefore, the information a particular user views can be arranged and accessed in a more familiar, relevant, and useful manner, individual to that participant.

The presentation sub-system 42 manages the normalized data and information into a presentable format for participants 13. For example, the world-wide-web, being a popular destination for users of the internet, accepts output in HTML format, and is accessible by a conventional internet browser. It is appreciated, however, that such data may be presented in virtually any form to accommodate different access devices (for example, WAP for mobile devices).

A security sub-system 44 is shown in FIG. 2 integrated with the other sub-systems 20, 28, 34, 36, 38, 42. Security sub-system 44 maintains data security in several ways. First, one embodiment contemplates that the insurers' 11 data is maintained on its own on-site database, and is controlled by the insurers 11. Second, the insurers' 11 data is encrypted when it is routed from the insurers' 11 database to the connectivity sub-system 20 and, ultimately, the participants 13 when a request 22 is made. Third, the participants' 13 browser includes encryption to view or send data over the internet 12. Finally, internal security is built into the data processing system 10 to only allow users with need-to-know access to particular data, such as claims and referral information. For example, providers 14 may have access only to claims and referral information of their insurers, but not individual claim summaries of their patients. Similarly, the employers 16 may have access to only their employees' claims information, but not some personal information.

An example of an encryption method is the 128 bit Secure Sockets Layer (SSL) with a key certified by VeriSign, Inc. Such SSL encryption means that data traveling through the internet and to participants' 13 browser cannot be interpreted by anyone between those two locations. Encryption is also useful because of the storage of user passwords. There is no place that a user's password is saved or used by the system as traditional cleartext. From one of the participants' 13 browser through internet 12 and to one of the insurers' 11 computer or server, the password is protected by SSL. Once the password reaches the final destined server, a cryptographic algorithm converts the password to a protected format. No one, therefore, who has privileged access to the server or any of the back-end applications, can get any user passwords.

In addition, encryption is useful along the operative connection to an insurer's 11 database sets 4, 6, or 8 to the data processing system 10. It is contemplated, however, that insurers' 11 computers or servers (database sets 4, 6, or 8) may not need such encryption along this operative connection, if the connection is a true point-to-point connection. Also, this encryption can be implemented through hardware or software, a virtual private network (VPN), or through the use of encryption protocols in a database, for example.

There are several modes with which data can be restricted, even within and among the insurers 11 and participants 13 of system 2. For example, security sub-system 44 may restrict the actual data that a participant 13 may request or view from any of insurers 11. A health care organization, thus, may only view data that they have provided. For example, doctors may only view claim data for their own patients. Alternatively, security sub-system 44 may restrict access to participants 13 to allow access to only particular fields on a particular screen of any particular database. For example, if a screen listed dollar amounts for claims, employers may wish to restrict who is able to view those dollar amounts. Other users, therefore, like patients 18, might be able to see the rest of the claims, but not the dollar amounts. Still, further, security sub-system 44 may restrict which screens will be accessible to which users. This level of security defines which functionality is available to the user. For example, a patient 18 in system 2 may not be able to view the claim submittal screen submitted by provider 14 at all, but may view a diagnosis information or health plan administrative screen. Customizable security based on the interests of the user may be included as well. This security method allows either the insurers 11 or participants 13 to set the parameters of security for the examples described above. It is further contemplated that this tool may be an internet-based tool that could add logins to the system, as well as specify values and screens that a particular user has access to. It is still further contemplated that a portion or all of the security measures can be employed throughout data processing system 12.

An audit sub-system 46, like security sub-system 44, shown in FIG. 2, is also integrated with the other sub-systems 20, 28, 34, 36, 38, 42. Audit sub-system 46 tracks the operation of all sub-systems. The information generated from audit sub-system 46 allows an administrator to monitor the operation of system 2 for problems and marketing trends.

Figure 3:
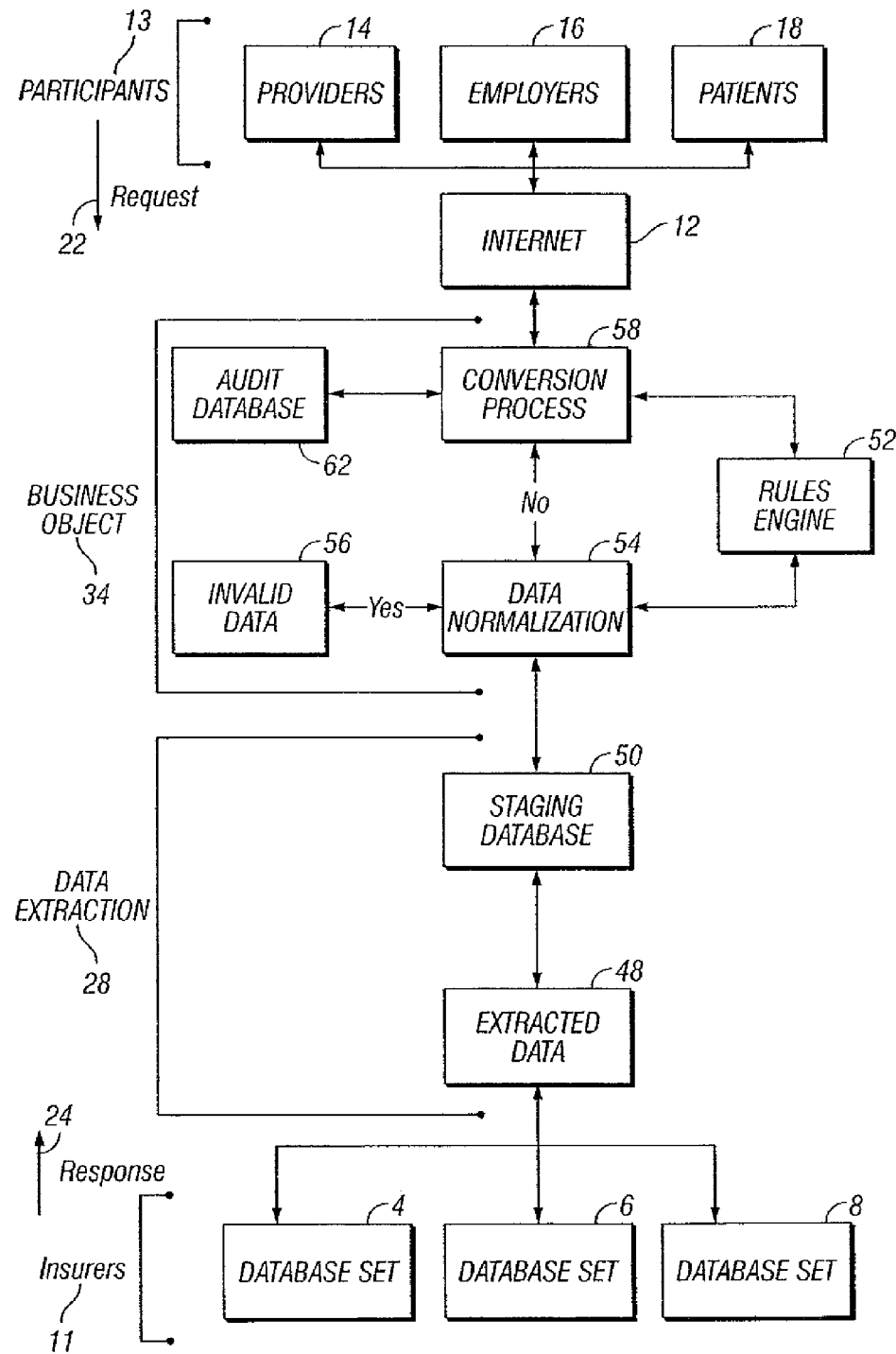
FIG. 3 is a diagrammatic view of the data extraction and business object sub-systems for the system of normalization shown in FIG. 1.

A diagrammatic view of the data extraction and business object sub-systems 28, 34, respectively, is shown in FIG. 3.

As previously discussed, the numerous databases represented by database sets 4, 6, 8 contain data in a variety of formats. Before the data is transferred to one of the participants 13, however, it is first formatted to a new format that is readable by any of the computers of participants 13, like HTML format, for example. The data is, therefore, "extracted" from the database sets, either 4, 6, or 8, and then "normalized" to be read by the computers of participants 13. The extracted data is indicated by reference numeral 48.

Extracted data 48 from either database sets 4, 6, or 8 is uploaded to a staging database 50 which is typically a portion of data extraction sub-system 28. Rules engine 52 serves a dual purpose of defining the rules that control the normalization of the data, as well as how the data, once normalized, is used. During the normalization process at 54, rules engine 52 homogenizes the data by determining what the data means, then inserting the data into the proper field as normalized data. Rules engine 52 also remodels the data, if necessary, to a structure or appearance predefined by the normalized format. As a simple example, in a referrals database that may hypothetically exist on database set 6, it may include the entry "New Jersey" in the state location field. If that field is requested by a participant 13, the rules engine 52 will cause that field to be extracted, then determine whether the meaning of this field corresponds to the meaning of the normalized state location field, and, if so, then convert the field to the normalized state location field at 58. Furthermore, if the rules engine 52 has predetermined that the normalized state location field should exist as only a two-character acronym, then the phrase "New Jersey" will be remodeled to the acronym "NJ." This is contrasted with traditional transliterating programs that would merely match the state location field of the referrals database with any field in another database titled "state location field" and then transfer the data. Such a program cannot determine the meanings of the state location fields, and then determine if their meanings matched, as well as not remodel the data to the appropriate appearance. For example, a field for laboratory enzymes might be expressed in Celsius in one database and in Fahrenheit in another database. Such data, as well as countless other data, are typically contextualized by the system they exist in. Transliterating programs do not compensate for such context among data. In the present disclosure, part of the normalization is determining the meaning of the data and locating it in a field of the same definition, but in a single format.

Rules engine 52 also determines whether the data is bad or invalid. Any bad or invalid data that is discovered during the normalization process at 54 is transferred to an invalid data database 56. Invalid data is placed in database 56 for review and appropriate corrective action and, if appropriate, reintroduced and normalized.

In addition, the rules engine 52 incorporates security 44 to determine whether the requestor has authorization to view the data that is being requested, as previously discussed. For example, if employer 16 requests claims data that illustratively exists on database set 8, the rules engine 52, in conjunction with the security 44, determines whether employer 16 has authorization to view the data subject of that request. If not, rules engine 52 would deny fulfillment of the request.

Once the data is converted and remodeled into the normalized format, rules engine 52 determines how the normalized data can be used. For example, if a request 22 is made from providers 14 to one of the insurers 11 to authorize a chest X-ray for one of the patients 18, a proper response 24 may reference data from various eligibility, claims, benefits, and personal data databases which rules engine 52 first extracts and normalizes. Once the data is normalized, rules engine 52 undertakes the process of responding to request 22. Rules engine 52 bases response 24 on predetermined rules established by the particular insurer 11 to determine whether a chest x-ray is an approved procedure in response to the request. It is contemplated that each insurer 11, or even each database set 4, 6, 8 can be subject to its own unique set of rules to govern any particular response 24.

An audit database 62, illustrated in FIG. 3, manages and maintains tracking information during the conversion process at 58. All data requests, responses, and e-commerce submissions can be monitored and recorded. This audit trail information is maintained in audit database 62 to enhance performance and security characteristics. It is contemplated that audit database 62 can be integrated with audit sub-system 46, as shown in FIG. 2, or database 62 can be a stand-alone system working independently or in addition to sub-system 46.

Figure 4:
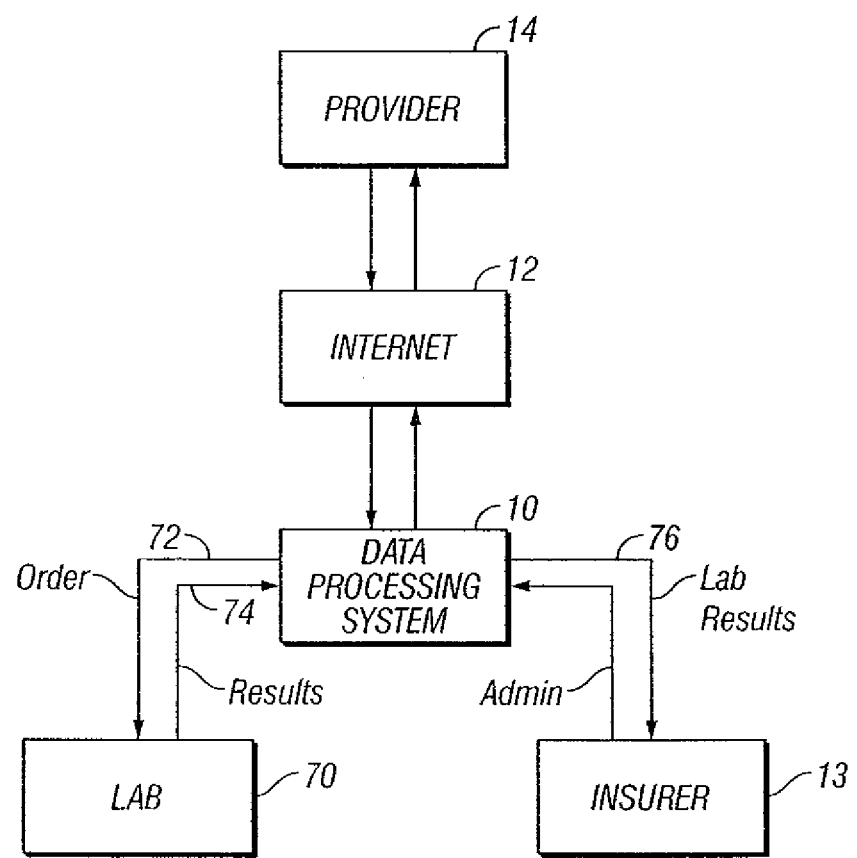
FIG. 4 is a diagrammatic view of a system of health care management for medical testing between health care insurers and participants.

In one embodiment of the disclosure, it is contemplated that system 2 will not only exchange information related to insurance and payment issues, but also provide active management of patient care. For example, as shown in FIG. 4, a portion of system 2 depicts the process for medical tests to be ordered, approved, and results submitted. For example, a health care provider 14, via the internet 12, places an order for a medical test. The order is transmitted through data processing system 10. The order is further transmitted at 72 to a laboratory 70, the order will disclose particular information that will be needed when either the specimen or the patient arrives. If a specimen is collected by provider 14, the order will identify the laboratory 70, and provide information to provider 14 so that the specimen may be marked accordingly before being sent to laboratory 70. Once laboratory 70 receives the order and the specimen, laboratory 70 can either communicate the status or results back through data processing system 10 to both the provider 14 and the appropriate insurer 13', as indicated by reference numerals 74, 76, respectfully.

Another illustrative embodiment comprises communication and transmission of healthcare data from a provider location to a plurality of healthcare plan payor locations. A problem is that current health care computer systems, particularly at the health care provider side, are not configured to batch distribute claims or other information electronically to more than one health plan. Typically, a provider office is affiliated with many health plans and must, therefore, design various internal office workflows in order to support the requirements of each health plan. Since the provider office also does not typically employ a large technology team that is capable of writing or installing different solutions to interface with all health plans that the office does business with, the provider must either hire this work out to service firms or augment staff to solve this problem. This disclosure assists in remedying this issue.

Figure 5:
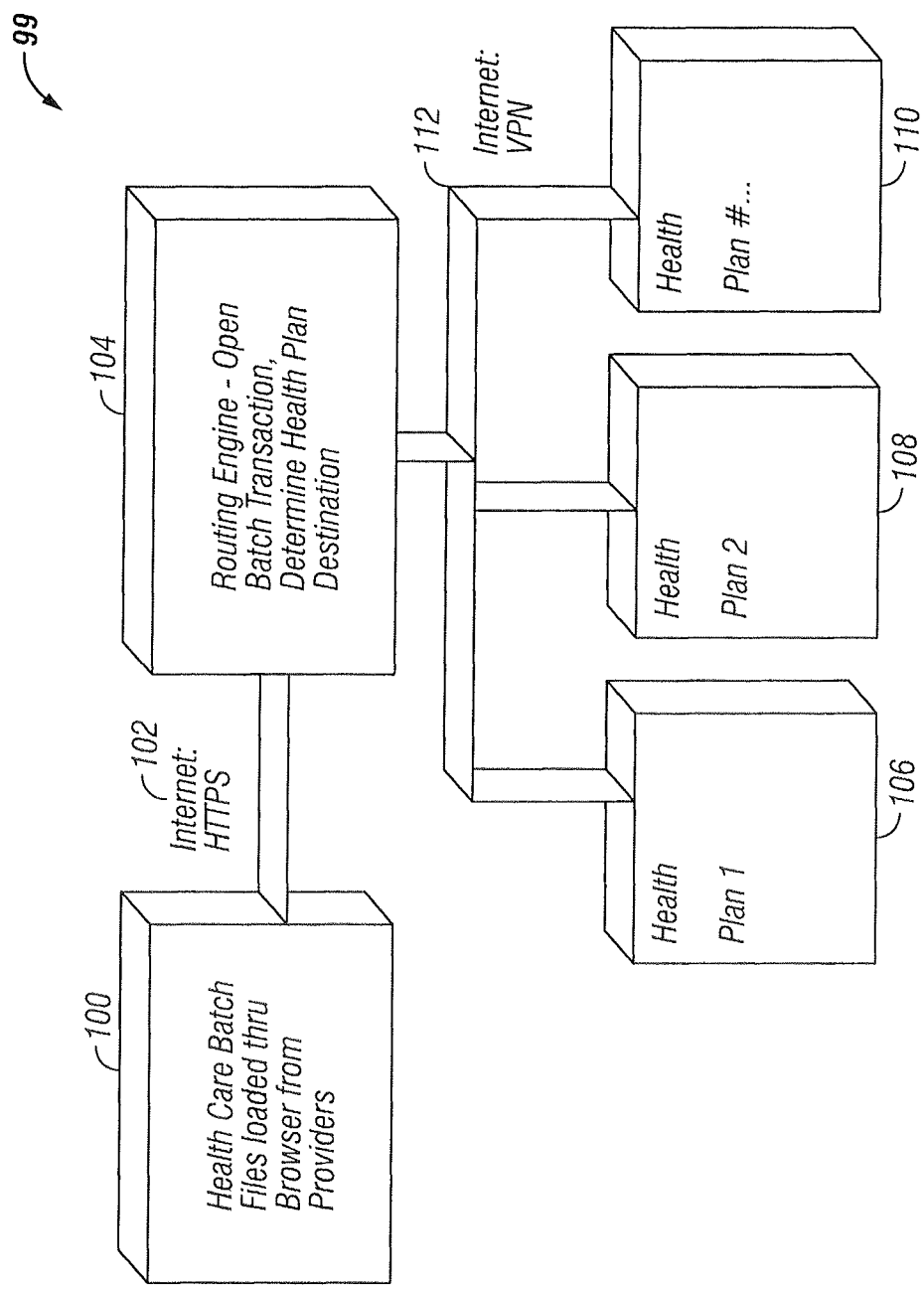
FIG. 5 is a flow chart showing another illustrative embodiment of the present disclosure including a routing engine that distributes data from a health care provider to health plans.

Accordingly, an illustrative embodiment as shown in FIG. 5, includes a transaction transfer system 99 between a health care provider computer 100, that transmits a file or data stream from their administrative system, or a plurality of healthcare payers, via Internet 102. The data file may include the data listed below related to claims, or may contain other information that is typical to healthcare data, as described previously herein.

Health Insurer Identification
Insured's ID Number
Patient Last Name
First Name
Middle Name
Patient's Address 1
Address 2
City
State
Zip
Patient's Phone
Birth Date
Gender
Relationship to Insured
Marital Status
Patient Employment Status
Condition Related to Job
Con. Rel. to Auto Accident
Cond. Rel. to Other Accident
Insured's Last Name
First Name
Middle Name
Gender
Birth Date
Insured's Address 1
Address 2
City
State
Zip
Phone
Insured's Group or FECA Number
Insured's Employer/School
Insured's Insurance Name
Referring Physician Name
Referring Physician ID
Outside Lab
Outside Lab Charges
Medicaid Resub Code
Medicaid Orig.
Prior Auth. Number
Diag Codes
Item
Date From
Date To
Place
Type
Procedure
Mod1
Mod2
DX Ind.
Charges
Days/Units
Patient
Provider
From Date
To Date
Diagnosis 1
Diagnosis 2
Diagnosis 3
Diagnosis 4
Procedure Line
CPT
Description
Amount
Dx pointer
Other Errors
Total Amount
Billed
Allowed Amount
Copay Amount
Withheld Amount
Writeoff Amount
Predicted Payment Files containing these fields can be separated into transactions. Transactions are individual units of work related to one entity that will either be accepting the information being passed, such as a payer, or an entity that will be sending the information, such as a provider. In this model, both standard (such as HIPAA X12) and non-standard files are uploaded into the internet portal, and then distributed from the portal to the individual health plans. Nonstandard files may be electronic data files that contain similar information to that defined in the HIPAA X12 transaction sets, except that the data in the file is either delimited by a special character (such as a comma or tab) or the data is formatted in XML (extensible markup language). Nonstandard files may also contain information that is not specifically related to published standard such as HIPPAA X12, HL7 or NCPDP, and in this case, the manner in which the information is organized into the file format is agreed upon between the sender and the receiver. An example of this might be Provider/Payor contract information, which typically defines the specialties, health care networks, and payment terms for the services that the provider performs on patients represented by the payer. This allows the healthcare provider to no longer break its information into smaller files or data streams for each health plan. Instead provider 100 sends all the related information to portal 104 which applies rules to the uploaded file in order to break the file into smaller transmissions to each individual health plan or payor. Portal 104 can be browser-based and secured via the https secure protocol. In this model, portal 104 can provide management of the entire "batch" or file that is uploaded. Illustratively portal 104 also provides status of each batch of transactions and whether they were successfully submitted to the individual health plans. The file is parsed into individual data elements based on the layout defined either by the standard, such as HIPAA X12, or by agreement on layout for non-standard files. Based on this layout, routing engine 116 also segregates the transactions for transmission to the individual health plans by the beginning and ending sections of each type of transaction. Individual data elements that uniquely identify the destination payer within the transaction are then identified and then compared against the configuration file to determine whether a valid electronic destination is available to send the transaction to. For example, a provider office might submit a standard X12 transaction file, such as a Health Care claims 837 file. That file contains all of the claims for patients seen that day, for all health plans. Once uploaded into the portal, the portal service reads the file, breaks the individual claims in the file into files that contain claims for each health plan and then transmits the file electronically to their respective health plan such as plans 106, 108, or 110 shown. The transmissions from the portal provider to the health plan can be conducted over an encrypted internet channel, such as a virtual private network (VPN) 112. The portal service then delivers the provider with a status of whether or not each smaller set of claims were successfully delivered to each health plan as well as an option to adjust any submissions that have failed.

Figure 6:
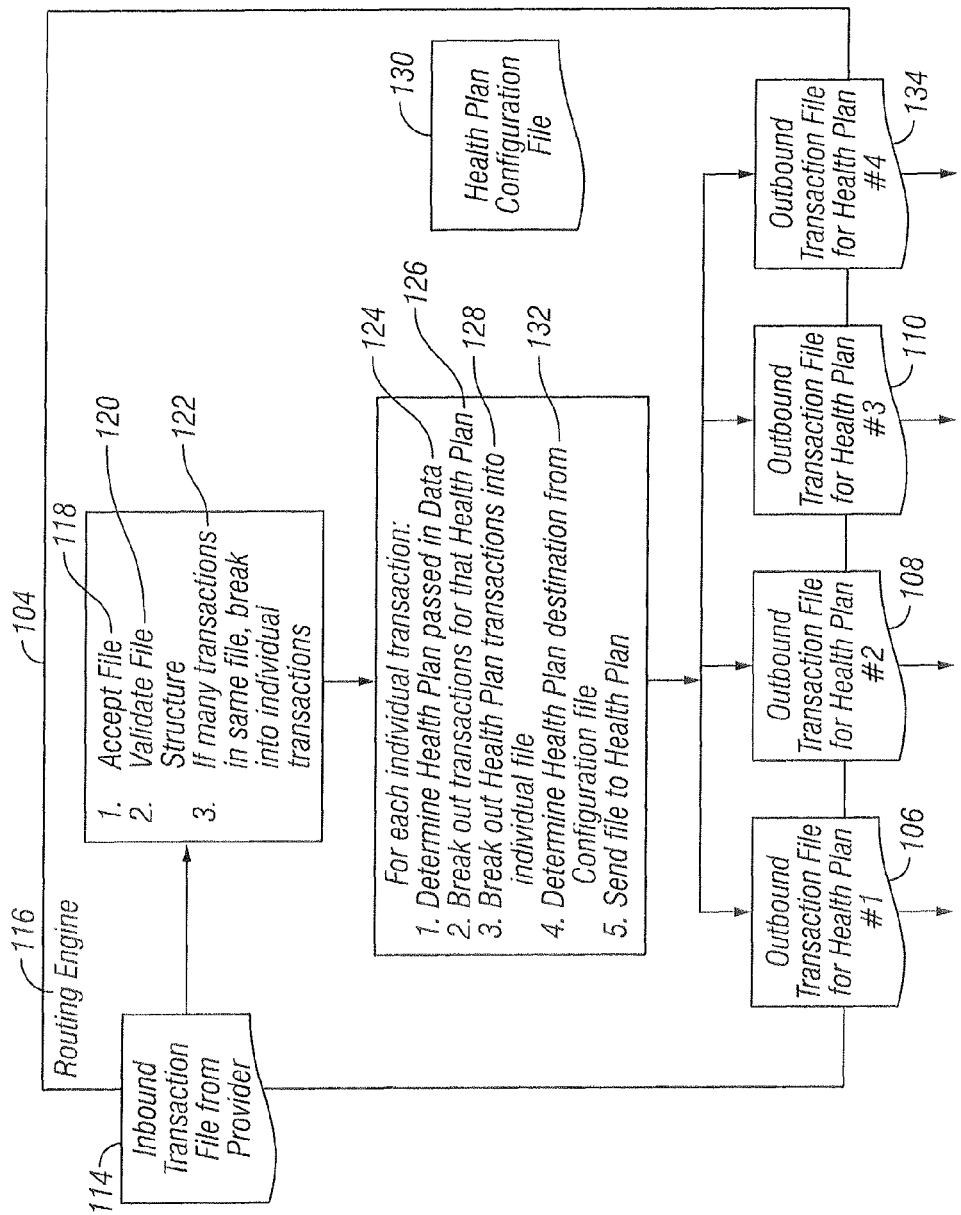
FIG. 6 is a chart showing the steps for distributing transaction file from a provider to a particular health plan.

The chart in FIG. 6 demonstrates the process of how portal 104 transfers an inbound transaction file from a provider to a plurality of different healthcare plans. As shown, portal 104 receives an inbound transaction 114 from provider system 100. A routing engine 116 begins processing the file by first accepting the file at 118, a predefined electronic address. This address at 118 may be a TCP/IP socket, port, or other electronic port. After receiving the file, it validates the file structure at 120 by reading through the file and comparing the structure to structure that is expected for the given file layout (as defined in either the standard transaction, such as HTPPAA X12, or the agreed format for non-standard files. The system then segregates multiple transactions received from the same file into individual transactions at 122. For file structures that are invalid or no destination address, the system keeps a record of the failures so that errors can be sent back to the sending entity. For each individual transaction, the destination payer is determined by inspecting a unique data item within the transaction at 124; breaking out individual transactions within each destination payer at 126; and creating individual files for each set of destination health plan transactions at 128. With this completed, the file is ready to be transferred to the payer or health plan. At this point, however, a health plan configuration file needs to be identified so the file knows where to go. In an illustrative embodiment, a health plan configuration file 130 is paired with its health plan transaction file at 132. The configuration file 130 is an electronic data file that identifies the electronic address for delivering information for each destination payer. This pairing identifies where the data file will be sent. With that, the file is transferred to the intended health plan recipient, either 106, 108, 110, or 134.

Figure 7:
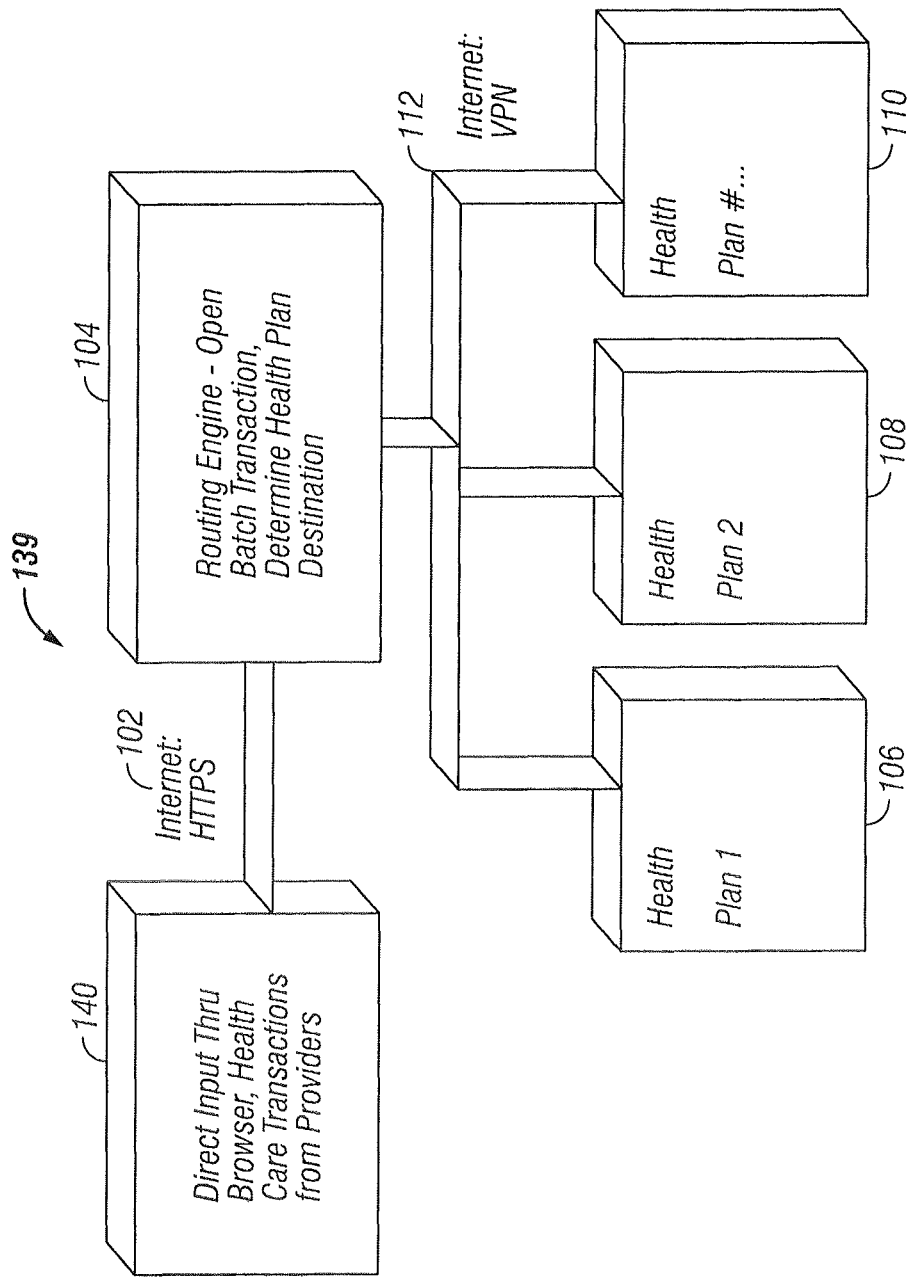
FIG. 7 is a chart showing another illustrative embodiment of routing a health care transaction from a provider to a health plan.

Another illustrative embodiment of a transaction transfer system 139 is shown in FIG. 7. This second model is similar to the first model, and may be used in conjunction with the first. Here, however, information from the health care provider at 140 is entered directly into a secure, internet portal 104, which is then placed into individual batches that are delivered from portal 104 to any of the health plans 106, 108, or 110 based on a routing engine 116 shown in FIG. 6 and previously described. This transmission can then be sent over a secure interne channel, such as a VPN 112. As with the first model, the portal can provide status of each batch of transaction and whether they were successfully submitted to the individual health plans.

Figure 8:
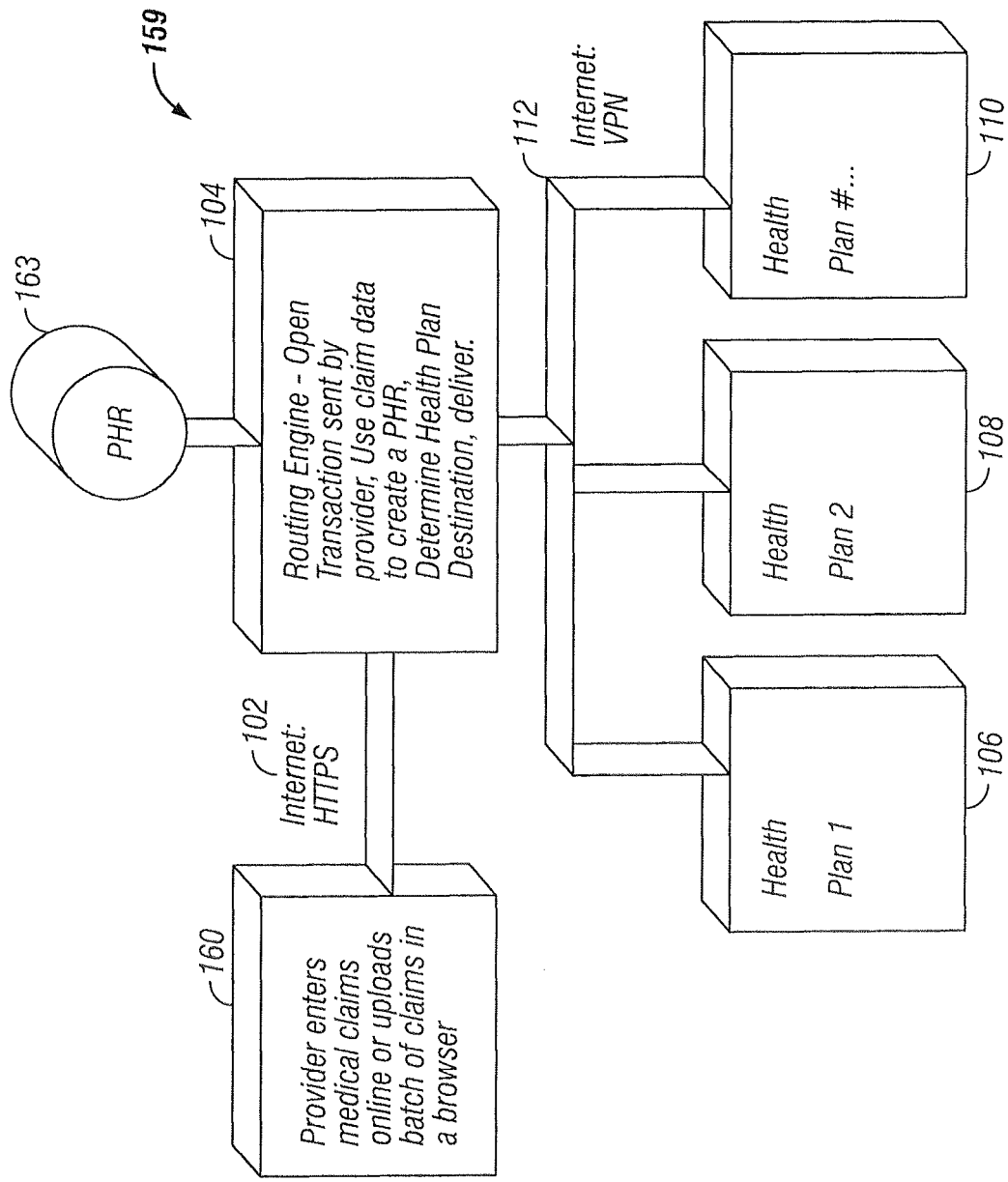
FIG. 8 is a chart showing another illustrative embodiment of the routing engine receiving data from the provider to be distributed to a particular health plan.

Another illustrative embodiment of a system 159 is shown in FIG. 8. This third model is a variation of systems 99 and 139 which can be used as a base to collect information. Just as in systems 99 and 139, providers securely transmit information to portal 104 such as healthcare claims from provider 160. This process can be accomplished either through direct data entry or through files and data streams from the provider's administrative information systems. As the rules are executed to determine which destination payer to send the health care information to, previously discussed, others rules are also applied to derive information from the provider-submitted data. For example, the diagnosis information may be pulled from a given transaction that contains claims information. Within this individual transaction, the diagnosis information on the claim can be evaluated, and then using this and other data in the transaction a new transaction for an Illness/Condition list can be created in a Personal or Electronic Health Record 162. The rules applied to the data are sufficient to extract patient demographic data, visit/encounter information, conditions and illnesses, surgeries and procedures, medication information, lab and other types of results, immunization information, clinical notes and summaries, such as discharge summaries. The data from the provider is transferred to the appropriate payer per the process previously discussed.

Although the system has been described with reference to particular means, materials and embodiments, from the foregoing description, one skilled in the art can easily ascertain the essential characteristics of the illustrative system and various changes and modifications may be made to adapt the various uses and characteristics without departing from the spirit and scope of the present invention as described by the claims which follow.

What is claimed is:

1. A computer system capable of transmitting healthcare data from a provider to a plurality of healthcare payors, the system comprising:
- a computer system that is in communication with at least one provider computer system and a plurality of healthcare payor computer systems;
- wherein the communication between the computer system and the at least one provider computer system and the plurality of healthcare payor computer systems is over the Internet;
- a routing engine on the computer system, wherein the routing engine is configured to receive uploaded healthcare transactions from the provider computer system in the form of a plurality of healthcare data in a data file;
- wherein the routing engine is further configured to validate the data file and determine whether there are multiple healthcare transactions in the data file and separate any of the multiple healthcare transactions into individual healthcare transactions;
- wherein the routing engine is configured to determine an identity of each healthcare payor computer system from the plurality of healthcare payor computer systems contained in the individual healthcare transactions;
- wherein the routing engine further comprises a healthcare payor configuration file that contains identities and routing addresses of the each healthcare payor computer system from the plurality of healthcare payor computer systems;
- wherein the healthcare payor configuration file is employed to pair the individual healthcare transactions with the routing addresses of corresponding healthcare payor computer systems of the each healthcare payor computer systems from the plurality of healthcare payor computer systems; and
- wherein the routing engine is configured to route the individual healthcare transactions to the corresponding healthcare payor computer systems over the Internet according to the routing address of the each healthcare payor computer system as a separate data file for each of the individual healthcare transactions.

2. The computer system of claim 1, wherein healthcare data from the provider is transmitted to the routing engine as the healthcare data is being entered by the provider; and wherein the healthcare data is then distributed to a corresponding payor.

3. The computer system of claim 1, wherein selected healthcare data is extracted from the data file to populate a personal or electronic health record.

4. The computer system of claim 3, wherein rules are applied to the selected healthcare data wherein the selected healthcare data is selected from the group consisting of at least one of demographic data, visit/encounter information, conditions and illnesses, surgeries and procedures, medication information, lab and other types of results, immunization infounation, clinical notes, summaries, and discharge summaries.

5. A computer system capable of transmitting healthcare data from a provider to a plurality of healthcare payors, the system comprising:
- a computer system that includes a routing engine that is in communication with at least one provider computer system and a plurality of healthcare payor computer systems;
- wherein the communication between the computer system and the at least one provider computer system and the plurality of healthcare payor computer systems is over the Internet;
- In the fifth to last line, please insert this after the word systems: over the Internet
- wherein the routing engine is configured to receive uploaded healthcare transactions in the form of a plurality of healthcare data in a data file from the provider computer system;
- wherein the routing engine is further configured to validate the data file and determine whether there are multiple healthcare transactions in the data file and separate any of the multiple healthcare transactions into individual healthcare transactions;
- wherein the routing engine is configured to determine an identity of each healthcare payor computer system from the plurality of healthcare payor computer systems contained in the individual healthcare transactions;
- wherein the routing engine further comprises a healthcare payor configuration file that contains identities and routing addresses of the each healthcare payor computer system from the plurality of healthcare payor computer systems;
- wherein the healthcare payor configuration file is employed to pair the individual healthcare transactions with the routing addresses of corresponding healthcare payor computer systems of the each healthcare payor computer systems from the plurality of healthcare payor computer systems; and
- wherein the routing engine is configured to route the individual healthcare transactions to the corresponding healthcare payor computer systems according to the routing address of the each healthcare payor computer system, as a separate data file for each of the individual healthcare transactions; and
- wherein the individual healthcare transactions are selected from the group consisting of eligibility, status of claim and explanation of benefits.

* * * * *

UNITED STATES PATENT AND TRADEMARK OFFICE
CERTIFICATE OF CORRECTION

| | | |
|---|---|---|
| PATENT NO. | : 8,639,531 B2 | Page 1 of 1 |
| APPLICATION NO. | : 12/760794 | |
| DATED | : January 28, 2014 | |
| INVENTOR(S) | : Malik M. Hasan and J. Dominic Wallen | |

It is certified that error appears in the above-identified patent and that said Letters Patent is hereby corrected as shown below:

In the Claims

Claim 5, please delete the text appearing in column 24, lines 17 and 18:

"In the fifth to last line, please insert this after the word systems: over the Internet"

Signed and Sealed this
Eleventh Day of November, 2014

Michelle K. Lee
*Deputy Director of the United States Patent and Trademark Office*